United States Patent [19]

Hartman

[11] Patent Number: 4,592,089
[45] Date of Patent: May 27, 1986

[54] ELECTROPHORETOGRAM ANALYTICAL IMAGE PROCESSING SYSTEM

[75] Inventor: John R. Hartman, Ann Arbor, Mich.

[73] Assignee: Bio Image Corporation, Ann Arbor, Mich.

[21] Appl. No.: 523,449

[22] Filed: Aug. 15, 1983

[51] Int. Cl.$^4$ ............................................. G06K 9/00
[52] U.S. Cl. ........................................ 382/6; 358/93; 358/107; 382/48
[58] Field of Search ...................... 358/93, 107; 382/6, 382/48; 340/706-710

[56] References Cited

U.S. PATENT DOCUMENTS 4,167,729  9/1979  Christenson et al. ............... 340/709
4,389,670  6/1983  Davidson et al. .................... 358/107

OTHER PUBLICATIONS

Taylor et al., "Design and Implementation of a Prototype Human Protein Index", Clinical Chemistry, vol. 28, No. 4, (1982).
Lester et al., "Computer-Assisted Analysis of Two-Dimensional Electrophoresis of Human Lymphoid Cells", Clinical Chemistry, vol. 26, No. 10, (1980).
Bossinger et al., "Quantitative Analysis of Two-Dimensional Electrophoretograms", Journal of Biological Chemistry, vol. 254, No. 16, (1979).
Kronberg et al., "Photometric Evaluation of Slab Gels", *Electrophoresis*, pp. 27-32, (1980).
Adams et al., "A Unique Silver Staining Procedure for Color Characterization of Polypeptides", in: *Electrophoresis*, (1981), Allen et al. (Eds.), Walter deGruyter and Company, pp. 155-167.
Vincent et al., "Multispectral Digital Image Analysis of Color Two-Dimensional Electrophoretograms", presented at Electrophoresis '81 Symposium, Apr. 8, 1981.

*Primary Examiner*—Leo H. Boudreau
*Attorney, Agent, or Firm*—Harness, Dickey & Pierce

[57] ABSTRACT

An analytical image processing system is used to analyze spots on color electrophoretograms. In one embodiment, the boundary of a spot chosen by the user is uniquely defined using polar cross-sections and is illustrated on a user interactive display. In such manner, the user is provided with visual confirmation of the shape of the spot used as a basis for generating output data relating to the spot analysis. The output data includes information not only about the two-dimensional area of the spot but also the intensity thereof to provide a useful measure of the quantity of protein present in the spot.

15 Claims, 27 Drawing Figures

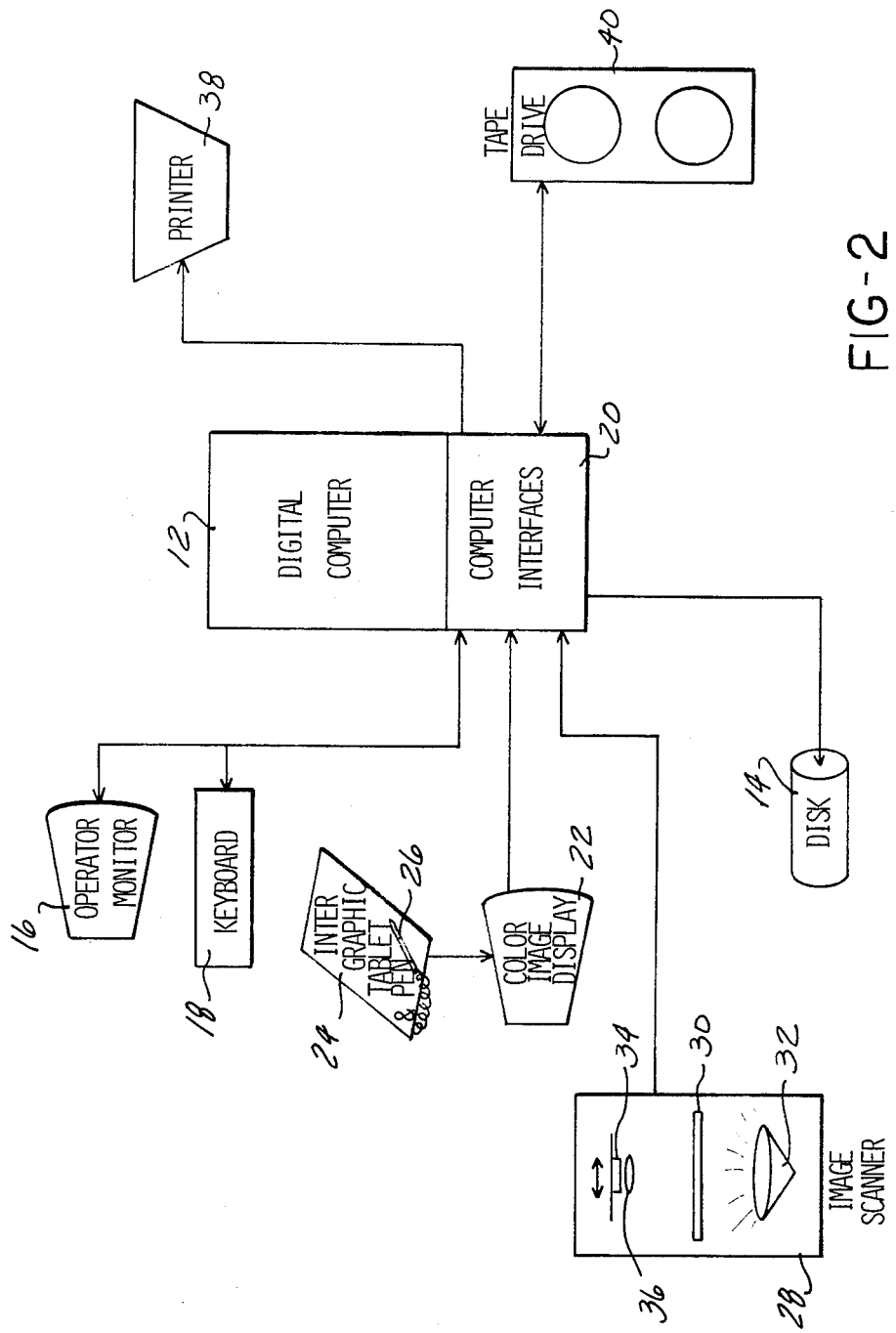

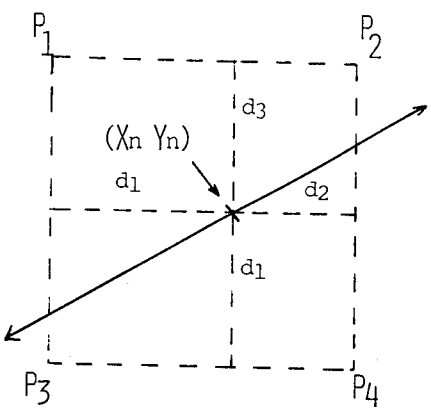
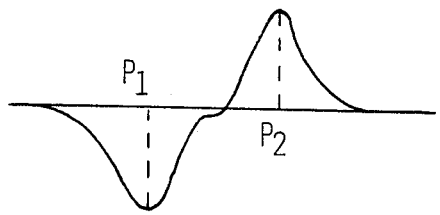
FIG-10
FIG-9
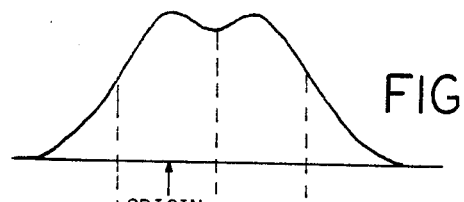
FIG-11A
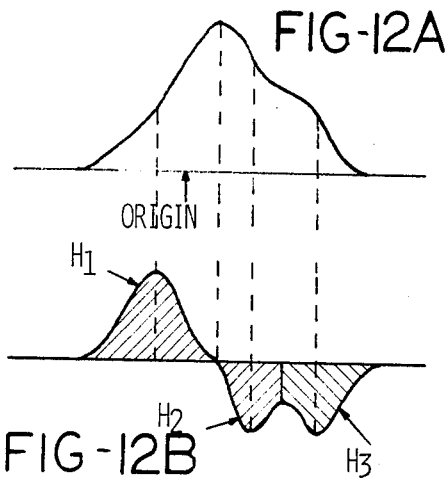
FIG-12A
FIG-11B
FIG-12B
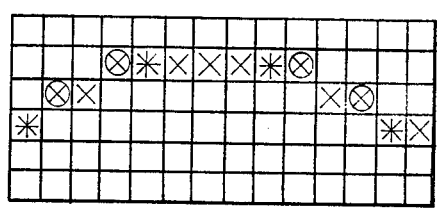
FIG-13
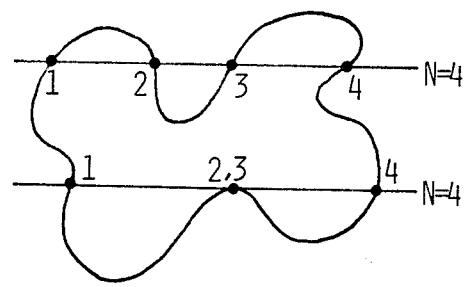
FIG-14

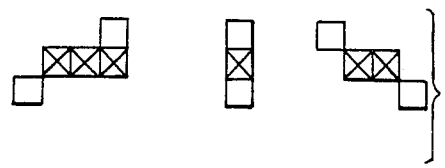
FIG-15A
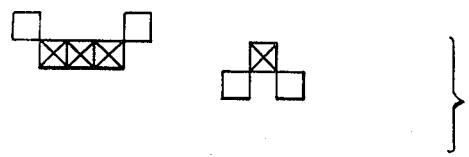
FIG-15B
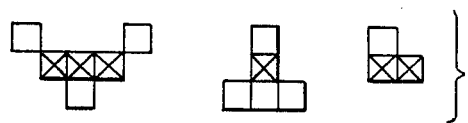
FIG-15C
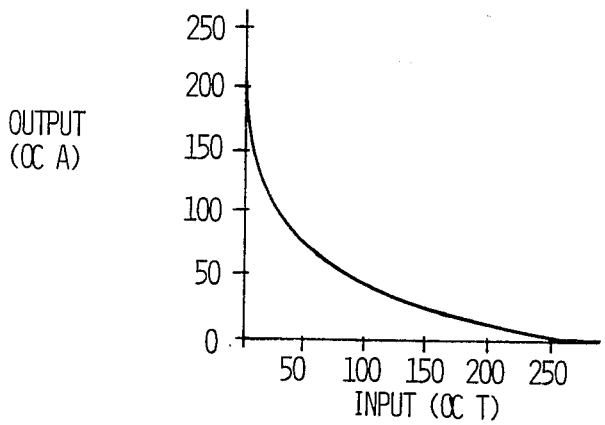
FIG-16A
| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| | -1 | 6 | 9 | -2 | 4 | 10 | 12 | 13 | -3 | 3 | 14 | -4 | 2 | 15 |
FIG-16B
FIG-17

ELECTROPHORETOGRAM ANALYTICAL IMAGE PROCESSING SYSTEM

DESCRIPTION

1. Technical Field

This invention relates to image analyzer systems and, more particularly, to systems for analyzing images of electrophoresis gels.

2. Background Art

The study of electrophoresis gels has provided a powerful tool for generating information about physical and chemical characteristics of protein gene products to the researcher. The proteins are characterized in the gel by spots. A typical gel will contain thousands of spots. The complexity of the task of obtaining information about selected spots in these gels has led to the development of computerized analyzing systems to aid the researcher. The technical literature discloses a variety of known techniques for analyzing electrophoresis gels. Representative, although certainly not exhaustive, examples of prior art systems are found in the disclosures in: Taylor et al, "Design and Implementation of a Prototype Human Protein Index", Clinical Chemistry, Vol. 28, No. 4, (1982); Lester et al, "Computer-Assisted Analysis of Two-Dimensional Electrophoresis of Human Lymphoid Cells", Clinical Chemistry, Vol. 26, No. 10, (1980); Bossinger et al, "Quantitative Analysis of Two-Dimensional Electrophoretograms", Journal of Biological Chemistry, Vol. 254, No. 16 (1979); Kronberg et al, "Photometric Evaluation of Slab Gels", *Electrophoresis*, Pages 27–32 (1980).

In general, the prior art systems are designed to operate on electrophoretograms in the form of digital images consisting of a matrix of pixel values. The electrophoretogram image is displayed on a user interactive display and the researcher is provided with some means for identifying the spot or spots to be analyzed. Unfortunately, it has heretofore been difficult to automatically define the boundary of the spot to be analyzed. Quite often there is no clear demarcation between the spot and its surrounding background using conventional boundary determination techniques. Consequently, the researcher may be misled as to the results of the analysis since the system may erroneously utilize pixel values which do not represent valid protein information about the desired spot to form a basis for generating its analytical output data. Thus, there exists a need for providing visual confirmation to the user as to the exact boundaries of the spot pixel values that were used during the analysis.

A color silver staining methodology for processing electrophoresis gels has been recently developed. The color staining provides the spots with polychromatic features or multispectral signatures that may provide additional descriptors of the proteins that provide the researcher with still further parameters that may be studied. A more detailed description of this color silver stained methodology is found in Adams et al, "A Unique Silver Staining Procedure for Color Characterization of Polypeptides", in: *Electrophoresis*, (1981), Allen et al (Eds.), Walter deGruyter and Company, Pages 155–167. The original color silver stain is marketed under the trademark "Gelcode" by Upjohn Diagnostics Division of the Upjohn Company.

Digital image analysis of color electrophoretograms is expected to enhance the users research capability as reported by Vincent et al in a paper entitled "Multispectral Digital Image Analysis of Color Two-Dimensional Electrophoretograms" presented at Electrophoresis '81 Symposium, Apr. 8, 1981. Digital image analysis of color electrophoretograms poses a somewhat different set of problems to the analytical imaging system designer than with conventional monochromatic gels. For example, it is often difficult to distinguish between background and spot pixel values for some colors. Consequently, it is difficult to identify reliable boundaries for faint spots and to provide accurate analytical information relating to them. In addition to monitoring the coordinate positions of the spots and the color thereof, it is important to provide an analysis relating to the quantity of protein associated with the spots. Quantity of protein is a significant parameter in characterizing protein gene expression in electrophoresis gels. Many of the known analyzer systems provide an indication of only the two-dimensional surface area of the spot as an indicator of protein quantity. While this information is useful, a more detailed analysis of spot protein quantity is desired.

The present invention is directed to solving one or more of these problems.

DISCLOSURE OF THE INVENTION

The present invention incorporates several different features that may be used separately or combined together to provide an extremely powerful analytical image processing system for analyzing color electrophoresis gels. The gels are scanned and stored as electrophoretograms in the form of matrices of gray level pixel values. In the preferred embodiment, a multichannel image is acquired with the digital pixel values in each channel resulting from light absorbance through color or interference filters passing different wavelengths.

The three color image channels are superimposed on a user interactive display to illustrate the gel as a color image. The operator moves a cursor to within the general visual boundary of a spot to be analyzed. The system will define the boundary or edges of the spot as a function of characteristics of pixel values adjacent the cursor. The pixel values within this defined spot boundary are analyzed and output data is generated relating to the results of the analysis. The system defined boundary of the spot is shown on the video display to thereby provide visual confirmation to the user that the data corresponds to the shape of the spot that the user desires to be analyzed.

A novel approach to defining the spot boundary is also employed in the preferred embodiment. A number of polar cross-sections passing through the spot origin at regular angular intervals are extracted from a predetermined image channel. As will be explained in detail herein, these polar cross-sections are used to accurately detect endpoints of the spot boundary.

In addition to providing other information about the spot, the system operates to calculate the intensity or density of the spot. The spot intensity is used as an additional parameter in expressing the quantity of protein associated with the spot. The spot intensity parameter is a function of the sum of the absolute difference between the pixel values and the background level in each channel for each of the pixels within the boundaries of the spot. Means are provided for overcoming the situation in which the pertinent spot pixel values are less than that of the background, such situation having a tendency to occur with spots of certain colors.

BRIEF DESCRIPTION OF THE DRAWINGS

These and other advantages of the present invention will become apparent to those skilled in the art upon reading the following specification and by reference to the drawings in which:

FIG. 2 is a block diagram of the system components;

FIG. 9 is a graph illustrating the interpolation of a point on a polar cross-section;

FIG. 10 is a sample of a derivative curve of a polar cross-section;

FIG. 11(a) is a profile of another polar cross-section typical of the situation where there are two overlapped spots, FIG. 11(b) illustrating a derivative curve thereof;

FIG. 12(a) is a profile of still another polar cross-section where spots are severely overlapped, with FIG. 12(b) being a derivative curve thereof;

FIG. 13 is a view illustrating the completion of the spot boundary after the endpoints on the polar cross-sections have been selected;

FIGS. 14, 15(A-C) and 16(A-B) are views helpful in understanding the boundary determination process according to the teachings of the preferred embodiment;

FIG. 17 is a graph illustrating the relationship of absorbance pixel values to those of the initial input pixel values associated with transmittance;

DESCRIPTION OF THE PREFERRED EMBODIMENT

A. System Hardware

Figure 1:
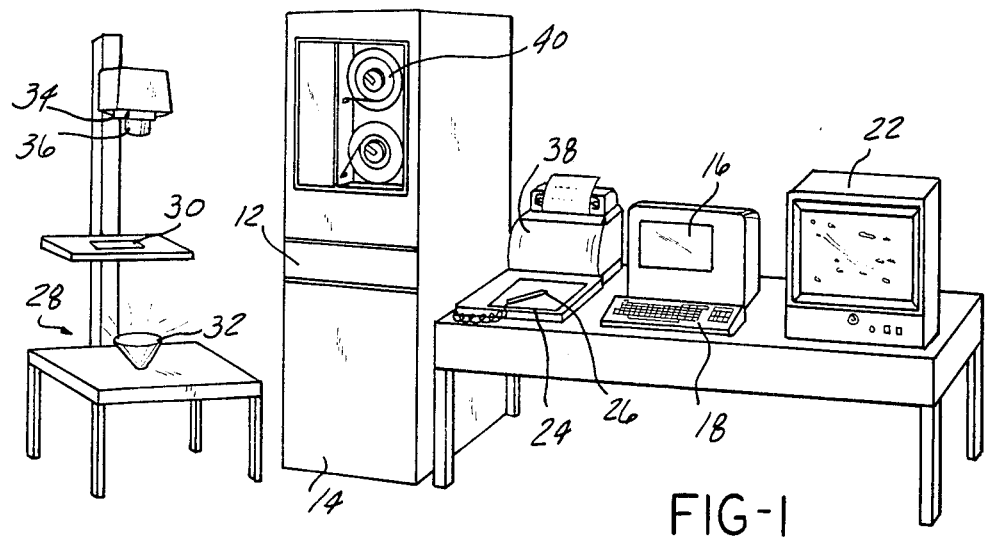
FIG. 1 is a perspective view illustrating hardware components making up the analytical image processing system of the preferred embodiment.

FIGS. 1 and 2 illustrate the various hardware components making up analytical image processing system 10 in pictoral and schematic form, respectively. It should be noted from the outset that while the preferred embodiment of this invention will be described in connection with analyzing color electrophoretograms, various features thereof also have applicability to black and white electrophoretograms as well.

System 10 employs a digital computer or central processing unit 12 for carrying out preprogrammed instructions. These instructions are contained in software routines stored in an external storage device such as disk memory 14. Disk 14 provides a high-capacity memory that can be quickly accessed by processor 12 in a manner known in the art. Pertinent software routines are loaded into processor 12 when needed in a manner known in the art. The specific syntax of the software routine will vary depending upon the nature of processor 12. A skilled programmer should be able to readily write suitable software routines compatible with the specific make of processor 12 to carry out the functions that will be described in detail herein. Consequently, inclusion of the specific software instructions herein would not be necessary for the skilled practitioner to make and use this invention.

An operator terminal includes a monitor 16 and keyboard 18 communicating with processor 12 via interface 20. Among other things, monitor 16 is used to display prompts from processor 12 to provide visual indications of commands entered via keyboard 18, results of analysis and the like.

A user interactive subsystem is provided by way of a color image display 22 communicating with an interactive graphic tablet 24. Tablet 24 includes a magnetic pen 26 which when touched against tablet 24, operates to generate electrical control signals. The most pertinent of these control signals is the positioning of a cross hair or cursor at desired locations on display 22. Other methods of positioning a cursor, of course, are well known in the art.

An image scanner 28 is used to generate digital images of an electrophoresis gel schematically illustrated by the reference numeral 30. In general, scanner 28 employs a light source 32 for illuminating gel 30 and a sensor element 34 which sequentially scans gel 30 and generates digital signals or pixels having values associated with characteristics of particular points on the gel. In the preferred embodiment scanner 28 is an Eikonix-scan 78/99 image digitizer commercially available from Eikonix Corporation. It employs a linear photo diode array as the sensing element which is stepped across the gel to generate the image matrix. To analyze the spectral characteristics of color silver stained gels, composite images may be formed using various color filters 36 as will be explained in more detail later herein.

Rounding out system 10 there is provided a printer 38 and a tape drive 40. Printer 38 may be used to provide a hard copy of the data generated as a result of analysis. The output data may also be displayed on monitor 16 and stored in external memory for later retrieval if desired.

B. Electrophoretogram Image Acquisition

Scanning of the gel 30 is initiated by an appropriate command provided by the user via keyboard 18. The user may enter recordkeeping data such as the name of the gel or number, the date it was created and the date of processing.

As high intensity light passes through the wet color silver stained gel 30 linear array 34 receives the transmitted light. By making discrete steps across the gel 30, a complete digital image is acquired. In this example, the digital image consists of 2,048×2,048 digital values per channel. Complete color digital information is obtained by scanning the gel three times. The first scan utilizes a red filter, the second scan uses a green filter and the third scan a blue filter. Each of the digital images will be referred to as a channel. Each channel contains a matrix of gray scale pixel values ranging in value from 0 to 255. Preferably each pixel value is a function of the absorbance as compared to the transmittance of light through the gel. For an 8"×8" electrophoretogram images acquired in this manner exhibit a resolution of about 100 micrometers per pixel. To reduce the amount of data in the analytical process and improve processing speed while maintaining adequate resolution, the 2,048×2,048 image of each channel may be reduced to a 1,024×1,024 image utilizing suitable digital filtering processes.

Each image channel is stored either on disc 14 or tape drive 40. Preferably, the image matrices are stored on disc 14 when the user desires to immediately enter into the spot parameter acquisition process as will now be described.

C. Spot selection, quantification and visual confirmation

Figure 3:
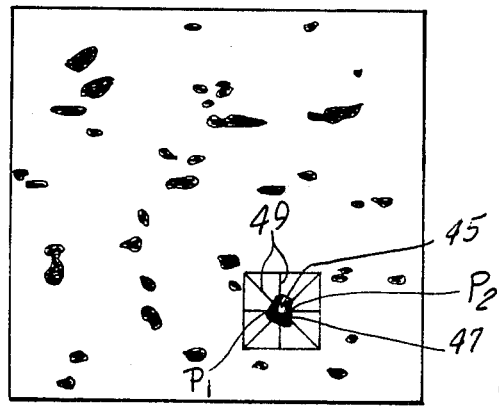
FIG. 3 is a view illustrating an electrophoretogram image in simplified form, part of which shows a cursor located within the visual outlines of a selected spot.

In this mode of operation the electrophoretogram color image is displayed on display 22. As noted above the color image is a composite of the three image channels. The color image is formed basically by superimposing the three image channels on display 22 to form a polychromatic image of the electrophoretogram thereon. FIG. 3 illustrates, in simplified form, an electrophoretogram image having a plurality of polypeptide spots thereon. However, it should be realized that the actual image is usually far more complex.

Figure 5:
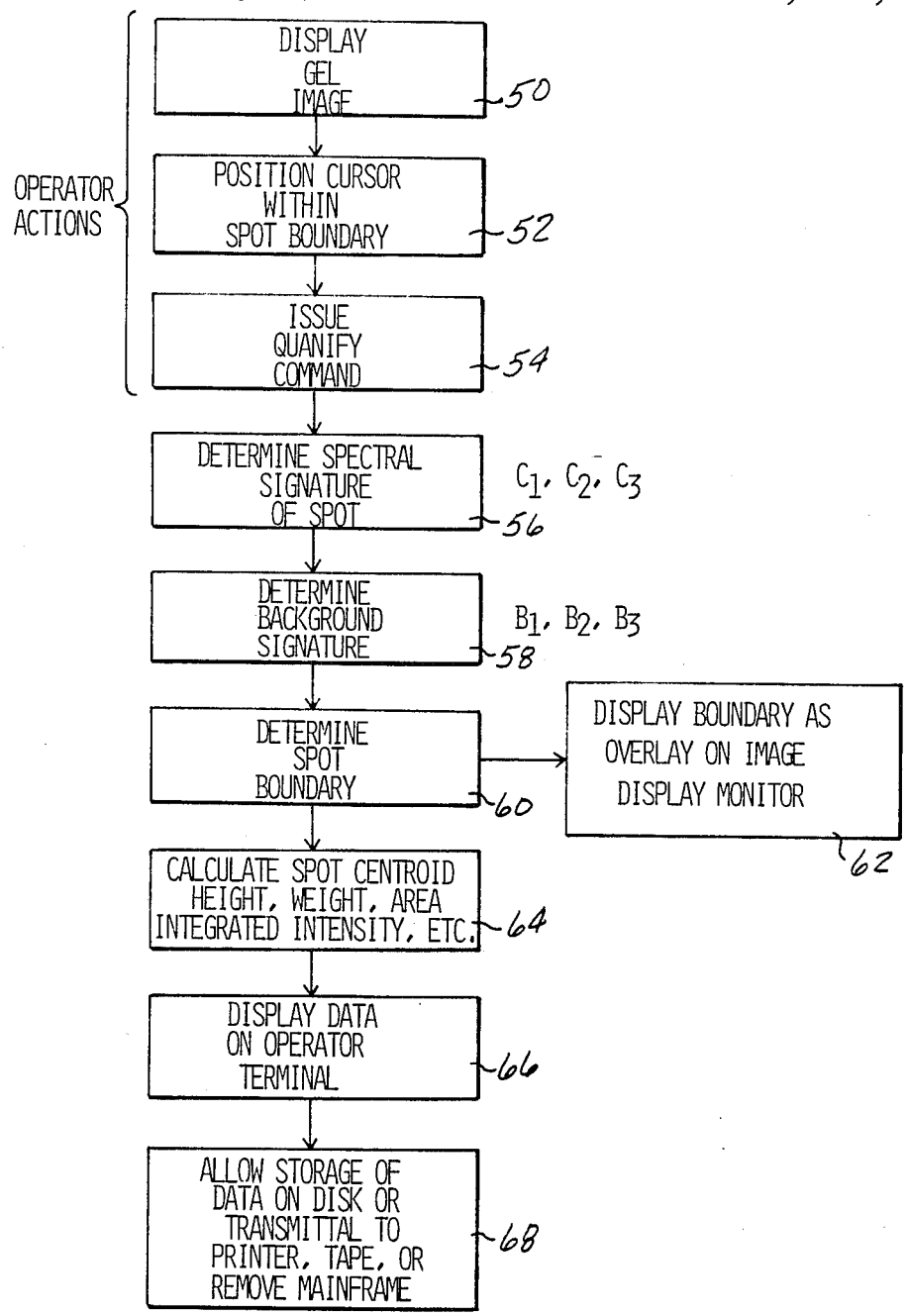
FIG. 5 is a flowchart showing the sequence of steps carried out in the analysis of the select spot.

FIG. 5 is a flowchart illustrating the sequence of steps during this mode of operation. After the gel image has been displayed, the operator uses the magnetic pen 26 and interactive tablet 24 to position a cursor 45 within the visual outline of a spot that he desires to analyze. The positioning of cursor 45 is shown in FIG. 3. Once the desired spot has been identified by the user, he enters a command via keyboard 18 to processor 12. Processor 12 responds to this command by entering into routines for finding the boundary edges of the selected spot. The system 10 thus automatically defines the boundary of the chosen spot as a function of characteristics of the pixel value adjacent the location of cursor 45. This automatic boundary definition technique will be described in detail later herein.

As illustrated in step 64 of the flowchart, processor 12 calculates the center of gravity or centroid of the two-dimensional spots whose boundaries have been previously defined by the system. In addition, the height, width, and area of the spot is also calculated. As will be described later in more detail, processor 12 also analyzes each image channel to provide output data associated with the spectral signature of the middle of the selected spot adjacent cursor 45 and the background of the image within a predefined area surrounding the spot. These signatures are referred to in Table I as central and background signatures, respectively.

Pursuant to another feature of this invention an additional parameter is analyzed which is associated with the protein quantity of the chosen spot. Each image channel is analyzed to derive a value associated with the intensity of the pixels within the defined spot boundary. This is referred to in Table I as the integrated intensity value. More will be said about the integrated intensity value later herein.

An example of the output data generated by processor 12 during the analysis of the chosen spot is presented in Table I which follows:

TABLE 1

| Gel: T17678 | Prepared: | 02-Sep-82 | Spot: (Protein |
|---|---|---|---|

TABLE 1-continued

| | Analyzed: | 07-Sep-82 | SEG CHAN: | Name) 1 REB:100 GBW:2 |
|---|---|---|---|---|
| Physical Characteristics: | | | | |
| Centroid (X,Y): 873,638 | | Height: 22 | Width: 19 | Area: 344 |
| Special Characteristics: | | CHANNEL 1 | CHANNEL 2 | CHANNEL 3 |
| Central Signature | | 41 | 24 | 45 |
| Background Signature | | 144 | 89 | 55 |
| Channel Integral | | 14076 | 15772 | 2601 |
| Integrated Intensity: 21312 | | | | |

The format is tabular and expresses four basic sections. The first section is bookkeeping information about the gel and spot selected. The other three sections are spot parameters, i.e. physical data derived from the analysis of the spot image. Spot physical characteristics are presented as: X and Y coordinate position of the spot centroid, maximum spot dimensions in the X and Y direction and spot area within the interpreted boundary. Color spectral information is presented in each of the three channels (red, green, and blue) for the spot centroid, gel background and spot intensity. The integrated intensity is a single number representing a three-channel quantitative expression of spot.

This data is displayed on operator monitor 16 and may optionally be printed out on printer 38.

Figure 4:
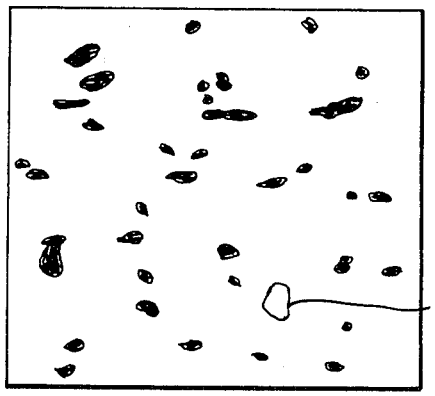
FIG. 4 is a view similar to FIG. 3 illustrating visual confirmation of the boundary of the selected spot.

Pursuant to one aspect of this invention, the system 10 provides a visual indication on display 22 of the spot boundary. As shown in FIG. 4, this is provided by changing all of the pixels within the system defined boundary to a given color. In practice this is accomplished by changing all the pixels to white on the display to highlight them. Other means for highlighting the boundaries, such as merely outlining the boundaries, can also be used.

The ability to illustrate the system defined spot boundaries is very important to the researcher. In such manner, he knows what pixels were actually used by the automated system as a basis to calculate the spot parameters shown in Table I. If desired the operator may prespecify a set of parameters which affects the sensitivity of the system boundary determination. However, the boundary and all spot parameters are always determined by consistent application of preprogrammed criteria thereby rendering the results objective and repeatable.

D. Analytical Processing Operations

1. Overview

The discussion that follows summarizes the methodology employed by the analysis system 10 for the segmentation (or boundary detection) and quantification of protein spots on two-dimensional gels. In short, protein spots are segmented by: (1) extracting a number of "polar cross-sections" passing through the spot origin at regular angular intervals, (2) determining the two "endpoints" on each cross-section that correspond to the boundaries of the spot from which it was extracted using extrema of the first derivative (or zero-crossings of the second) as the main criterion, and (3) interpreting these cross-section endpoints as vertices of a 2n-sided polygon, where n is the number of polar cross-sections extracted. In FIG. 3 there is shown a rectangle 47 surrounding the cursor-selected spot and a plurality of polar cross-sections 49 passing through the origin defined by the coordinates of cursor 45. As will be explained, system 10 operates on the polar cross-sections 49 to select endpoints $P_1$ and $P_2$ which are used to define the spot boundary contour.

Once a complete boundary contour has been determined for a spot, a measure of "intensity" can be integrated over all pixels within the boundary to yield an estimate of the quantity of protein present in the original spot. In the case of a monochrome gel image, which requires only a single channel for its digital representation, this pixel intensity measure is simply the optical density after subtraction of local background. The recent advent of color staining techniques in 2-D electrophoresis, however, has generated a need for quantification techniques adapted to the multichannel gel images that are required to preserve color information; it is, moreover, a property at least of the dominant silver stain method that spots may appear either less or more optically dense than background in any of the three image channels (representing red, green, and blue). Hence there exists the question not only of how to treat this measure when it becomes negative after background subtraction. The present invention has solved both problems with a measure—called, simply, "intensity"—that is essentially a weighted "distance" between the spectral "signature" of a pixel and the signature of local background in the three-dimensional space defined by the red, green, and blue channels; this is described in greater detail below.

Some of the motivations behind the use of the polar segmentation technique of this invention merit some discussion before its operation is described in detail. What might be called the "classical" approach to the spot segmentation problem involves the taking of horizontal cross-sections, each corresponding to a line in a gradient-transformed image, through a spot from top to bottom. This technique has the advantages of ideally requiring only one line of the image to be held in program memory at a time, and also of allowing all of the spots in an image (or image region) to be segmented in one "sweep" through the image through the use of sophisticated data reduction schemes. It also, however, has the disadvantage of being inadequate for quantitative work if spot topology and not gray-level thresholding is to be used to define spots and their boundaries. While the horizontal cross-sections near the centers of spots are well-behaved and yield distinct boundaries, this ceases to be the case near the vertical extremes of spots where the angle between the cross-sections and the tangent to the spot boundary becomes very acute. Endpoints of these cross-sections tend to be very unstable (where they can be found at all). Of course, this problem can be ameliorated by taking several vertical cross-sections to reconstruct the top and bottom, but this would unduly complicate the segmentation process while completely removing both of the advantages of the technique noted above. The problem reverses—but does not diminish—if horizontal cross-sections are taken of the raw image and subsequently differentiated. The detected boundary diverges from the true boundary because the former is based on extrema in the horizontal gradient and the latter in the two-dimensional gradient, which is the Euclidean sum of the horizontal and vertical gradients; i.e., $G = G^2_h + G^2_v$. It can be seen that $G_h$ is an adequate representation of G only near the vertical center of the spot where $G_v$ is near zero.

The polar segmentation technique avoids this problem because the polar cross-sections remain much more closely perpendicular (and exactly so, if the spot is circular with the "origin" at its center) to the boundary tangent along its entire perimeter. This rotationally-symmetric definition of the boundary criterion is highly desirable when accurate quantification is desired.

The series of processing steps that follows in Table II describes the overall operation of the segmentation and quantification algorithms in the system software. The names appearing at the left margin designate the routines that are responsible for executing the corresponding process. When asterisked(*), their functioning is described in greater detail in the text following this outline.

TABLE II

OVERVIEW OF SEGMENTATION/
QUANTIFICATION OPERATIONS

| | |
|---|---|
| | Get cursor position $X_c$, $Y_c$ |
| WINDIN | Input to memory 60 × 60 window centered about $X_c$, $Y_c$ for each of 3 channels |
| BCKSIG* | Determine Background signature (local) $B_i$; i = 1,2,3. |
| SPSIG | Determine Spot signature near $X_c$, $Y_c$: $S_i$; = 1,2,3. |
| SPTEST | Test MAX ([Bi—Si]) as indication of presence of spot. Exit with error if fails. |
| CHANSL | Select "segmentation channel" based on [Bi—Si] and noise. Generally, channel with maximum spot intensity is selected. Determine "orientation" of spot in segmentation channel; >0 if "above background", <0 if "below background". |
| MEDSM | Pass median filter over segmentation channel window to remove point noise without boundary smoothing; output to separate segmentation window. Determine width of spot as basis for selecting number of polar cross-sections to use in boundary determination. Sequence of steps: |
| POLSEC* | Extract horizontal CS through $X_c$, $Y_c$(i.e., polar CS @ * = 0) |
| CSDIF | Differentiate this CS |
| CSSMTH | Smooth resulting differential Cs |
| CSSEG* | Determine spot endpoints on CS. Spot width is the distance in pixels between spot endpoints or horizontal CS. If width >=16, PCS's will be taken every 10 degrees (i.e., 18 PCS's, 36 endpoints); otherwise every 20 degrees (9PCS's, 18 endpoints). For each PCS (0* = 10 degrees or * = 20 degrees): |
| POLSEC* | Extract polar CS at * |
| CSDIF | Differentiate |
| CSSMTH | Smooth differential Cs |
| CSSEG* | Determine and store PCS endpoints in terms of distance from $X_c$, $Y_c$ in pixels along PCS. Each endpoint defines the terminers of a spot "radius". If # of "missing" spot radii exceeds either (1) permissible maximum total or (2) permissible maximum consecutive, EXIT with error. |
| RFILL* | Fill missing radii by interpolation. |
| RADFLT* | Filter out "errant" spot radii using median technique - each radius must be a median of itself and 2 nearest neighbors. |
| POLRCT | Translate CS (radius) endpoints back to rectangular coordinates |
| PERIM* | Connect radius endpoints using linear interpolation to form contiguous spot boundary, and flag all resulting boundary pixels in segmentation window. [Thin spot boundary not implemented yet!] |
| CFILL* | Use boundary-filling algorithm to find all pixels within boundary contour and generate descriptor record to be held in memory that concisely specifies location of all such pixels. |
| QSPOT* | Generate statistics (AREA, INT. INTENSITY, |

| TABLE II-continued |
| --- |
| OVERVIEW OF SEGMENTATION/ QUANTIFICATION OPERATIONS |
| CHANNEL) (INTEGRALS) using all pixels specified by Spot Pixel Descriptor Record Output results to user terminal. |

2. Background Signature Determination (BCKSIG)

Whether spot quantification is done using optical density or a multispectral distance measure such as in the present invention, it is necessary to incorporate into it some measure of the brightness of background in the local area around a spot. This measure is the "background signature" and consists of a single number for monochrome and three numbers ($B_1$, $B_2$, $B_3$) for color images.

Figure 6A:
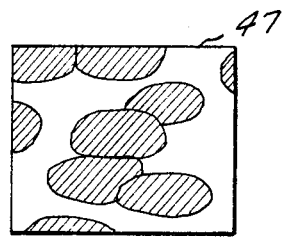
FIG. 6(a) represents a portion of an electrophoretogram image surrounding a selected spot, with FIG. 6(b) illustrating a histogram thereof.
Figure 6B:
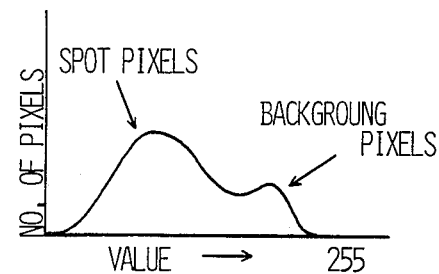

Ordinarily, the mode of a histogram of pixel values taken from an area of a gel image surrounding a spot will coincide with the background level near the spot. While the straightforward method of constructing a histogram and finding its mode will yield correct results in a majority of cases, it can and usually does break down in areas of a gel that are densely populated with spots, as in FIG. 6. In this case, the proportion of pixels represented in the histogram that are actually within spots may be great enough so that the histogram mode reflects the values of these pixels rather than pixels in the true background. More specifically, it is the "flat" regions in an image that contribute to sharp spikes in its histogram, and in an area crowded with spots the relatively flat regions near the centers of spots (and between overlapped spots) may outnumber the small enclaves of what is actually background.

Figure 7:
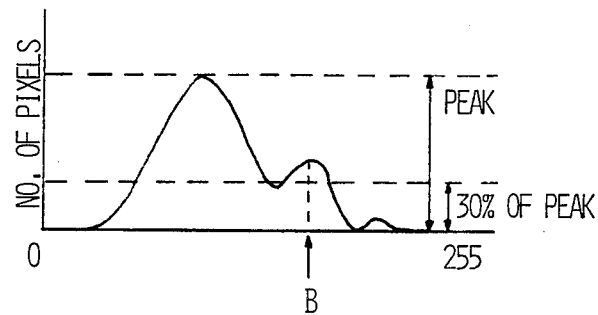
FIG. 7 is an example of another histogram illustrating selection of a background value for a given image channel.

For this reason, the background determination technique of the preferred embodiment gives preferential treatment to local peaks located on the "bright"—i.e., high transmittance—side of the histogram, even if this does not coincide with the histogram mode. In practice, the background value is determined as the highest pixel value in the histogram at which a local peak exists that is at least 30% of the height of the histogram mode (see FIG. 7). A local peak is operationally defined as a pixel value for which the number of pixels is greater than that of the four pixel values on either side of it.

In practice, the background signature for each image channel is calculated from a preselected area 47 surrounding cursor 45. The background signatures are compared with the spot signatures and that channel having the greatest difference therebetween is chosen as the "segmentation channel" for performing the segmentation or spot boundary determination steps that follow.

3. Spot Segmentation a. Extraction of Polar Cross-Sections (POLSEC).

The objective here is to obtain a one-dimensional array of data representing a cross-section through a selected rectangular area 49 surrounding the cursor selected spot at an arbitrary angle * to the horizontal. It is further desirable that a constant distance scale be preserved along the array regardless of the value of *. It is thus not an adequate approach to calculate the line $y = y_0 = (x-x_0)\tan*$ and subsequently sample every pixel that intersects it to some minimal extent. For example, if $* = */4$, the $n^{th}$ pixel in the cross-section array will lie at a distance from the origin that is 2 times that of the $n^{th}$ pixel in a horizontal or vertical cross-section. "Staircase" sampling patterns are also seen as potentially problematic, especially with smaller spots.

Figure 8:
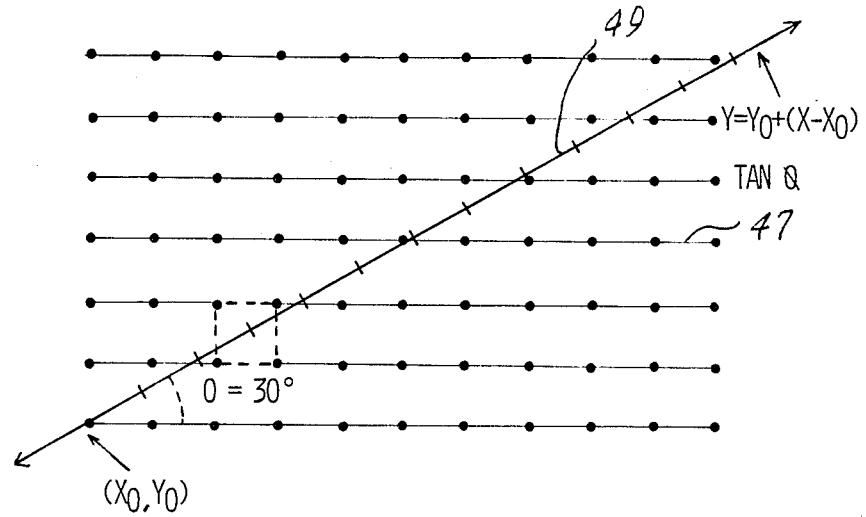
FIG. 8 is a graph illustrating the generation of a polar cross-section through a selected spot.

To avoid these pixel sampling problems altogether, an interpolative approach is taken that involves the calculation of the precise coordinates of successive points at distances on either side of the origin (defined by the position of cursor 45) of 1.0, 2.0, 3.0 . . . pixels along the line whose equation is given above. This is illustrated in FIG. 8 where *=30 degrees. Each dot in the matrix represents the center of a pixel. Values are interpolated from surrounding pixels for each of the points located at the marks along the polar cross-section. These coordinates are given by $x_n = s_o + n\cos*$ $y_n = y_o + n\sin*$ n=0, 1, 2 . . . In practice, it is not necessary to compute the trigonometric functions. Because of the complimentarity and symmetry properties of sines and cosines, and the fact that cross-sections are only taken at 10 degree intervals, we are able to rely on simple manipulations of a lookup table containing only 10 discrete values of sin* for *=0, 10, 20 . . . 90 degrees.

Finally, the value of the cross-section array at n is estimated using bilinear interpolation of the surrounding four discrete pixel values as shown in FIG. 8. The value of the point ($x_n$, $y_n$) is $d_y(d_1P_2 + d_2P_1) + d_3(d_1P_4 + d_2P_3)$ where $d_1$, $d_2$, $d_3$ and $d_4$ are the distances shown in FIG. 9.

b. Cross-Section Boundary Detection (CSSEG).

The polar cross-section is then differentiated and smoothed. Then, it is operated on by the CSSEG routing to determine the locations of spot edges on either side of the origin. In the case of a well-behaved, isolated spot, the differentiated cross section will have a profile much like that shown in FIG. 10 and the endpoints are easily located at points $P_1$ and $P_2$, corresponding to a "trough" on one side of the origin and a "peak" on the other. Which extremum to seek on a given side of the origin is determined by the orientation of the spot, which has been previously tested by the routine CHANSL.

The algorithm employed in CSSEG is actually somewhat more complex than this, as it is necessary to cope with gross spot overlap, image noise (which is amplified in the differentiation process), and morphological disturbances that often introduce small spurious inflections in spots, particularly very large ones. Furthermore, some situations—e.g., faint and overlapped spots—require very sensitive boundary detection, whereas the opposite is true for others, such as noise and morphological irregularities.

FIG. 11b illustrates how the differentiated CS can be interpreted as a sequence of "humps". A "hump" is defined as the area between a peak or trough and the zero line, with peaks and troughs being delimited by a zero-crossing or, respectively, by positive troughs and negative peaks. (An example of the latter delimiting criterion is shown in FIG. 12. The area of each hump is a measure of the strength or distinctness of the boundary that is potentially associated with it, and this affords the user a means of adjusting the sensitivity of boundary detection via a hump threshold $H_T$ or "rebound value" that specifies the minimum value a hump must attain to be considered a boundary. Referring to FIG. 10, with the origin located as shown, a low setting of $H_T$ (such that $H_T < H_2$) will cause a boundary to be detected at $P_2$, effectively resolving the overlapped spots. It is possible, though, that a situation similar to that in FIG. 11 (but perhaps less pronounced) is caused not by overlap but rather by stain or protein saturation in a single spot. In this case, $H_T$ would have to be set such that $H_2 < H_T < H_4$ to ignore the spurious boundary and detect the correct one at $P_2$. Of course, setting $H_T$ such that $H_T > H_4$ will result in no boundary at all being detected. In practice, setting the hump threshold to a value near zero (maximum sensitivity) works well for the vast majority of spots, and thus has been established as the default. In such manner the user can modify the system's criteria for defining the spot edge boundary to more closely match his visual analysis.

This process continues for a plurality of polar cross-sections. In this embodiment, eighteen cross-sections 49 are actually taken every 10 degrees if the spot width is greater than sixteen thereby resulting in thirty-six endpoints; otherwise nine cross-sections taken every 20 degrees are used.

c. Cleaning the Radius Endpoint Data (RFILL, RADFLT).

Following the completion of the boundary detection process on all of the differentiated polar cross-sections, we are left with an array of numbers that describe (in pixel units) the distances from the origin to the spot boundary for radii at angles from 0 degrees to 360 degrees in either 10 degree or 20 degree increments, depending on estimated spot size. Occasionally it happens that boundary detection fails for one or more of the radii, and it is the job of RFILL to correct this problem, provided that it doesn't exceed some maximum allowable severity. This is done simply by interpolating between adjacent valid (i.e., non-zero) radii. For example, if the radii from 20 degrees to 50 degrees are (14, 0, 0, 17), the missing (0) radii are replaced with the values 15 and 16. Maximums are enforced for both the number of consecutive missing radii and the total number of missing radii that may occur; these are currently set to 1/6 and ½ the total number of radii, respectively. Exceeding either one causes the analysis to abort with a corresponding error message.

The final "cleaning" step performed on the radii before they are converted back to their rectilinear image coordinates is a median filtering process (by RADFLT) that removes high-frequency—and presumably spurrious—irregularities from the spot boundary. This consists of nothing more than requiring that any radius be a median of itself and its two adjacent radii, and replacing any violating radius with the closest number to it that satisfies the median rule; in the radius sequence (..., 16, 16, 5, 18, 19, ...), for example, the 5 would be replaced with 16.

d. Completing the Boundary Contour (PERIM).

Once converted back to their rectilinear coordinates, the 18 or 36 radius endpoints define the vertices of a similarly-sided polygon that is used to approximate the spot shape. It is the function of PERIM to fill in the sides of this polygon, producing the closed and contiguous boundary contour that will later be required by the CFILL routine when it attempts to find all of the pixels in the interior of the spot. The algorithm used by PERIM (shown in FIG. 13) is a straightforward interpolation and requires little explanation except to note that whenever the interpolating line splits two pixels evenly, the one furthest from the spot origin is selected for inclusion in the boundary. In FIG. 13, the "*"s designate the original radius endpoints and the "x"s are the interpolated boundary pixels.

e. Finding Interior Pixels (CFILL).

The CFILL routine is responsible for converting a pixel map (i.e., the segmentation window) in which boundary pixels have been flagged into a concise and easily accessible data structure describing the locations of all pixels within the boundary.

To explain the algorithm employed by CFILL it is necessary to introduce the concept of boundary parity. This derives from the fact that a straight line passing through a plane closed curve will intersect the curve an even number of times if tangential encounters are counted as two intersections (see FIG. 14). It is further true that whenever the count of intersections changes, an odd or even result indicates the beginning or end of a segment of interior pixels, respectively. In order to implement this algorithm, it is necessary only to distinguish ordinary intersections from tangents. This is done in CFILL by considering horizontal stretches of boundary pixels and counting the number of "connections" above (A) and below (B) them. An intersection is then characterized by $A=1$ and $B=1$; a tangent by $A=0$, $B=2$ or $A=2$, $B=0$; and an illegal boundary configuration by anything else. FIG. 15 shows examples of each of these situations, respectively. Strictly speaking, the algorithm requires that every boundary pixel have exactly two neighbors on the boundary; this requirement is violated rather frequently, however—such as when the boundary takes a right-angle turn—and CFILL was thus designed to recover from certain specific situations that violate the 2-neighbor rule but nevertheless create no ambiguities in the interpretation of the boundary.

Since the boundary parity algorithm identifies horizontal stretches of interior pixels for each image line, it makes sense that the locations of these pixels be recorded this way. FIG. 16(a) shows the upper portion of a hypothetical spot boundary and illustrates how the interior pixel descriptor is built. The latter as shown in FIG. 16(b) is a one-dimensional array in which any negative number is taken as the negative of a line number in the image. Following each line number are one or more pairs of positive numbers designating the beginning and ending positions of an unbroken sequence of interior pixels. This descriptor array is made available to the routines QSPOT, which performs the quantification of the spot, and BNDWRT, which "whites out" all interior pixels on the monitor as confirmation to the user of the correctness of segmentation.

3. Spot Quantification (QSPOT)

The QSPOT routine uses the original image windows (for each channel) and the interior pixel descriptor array created previously by CFILL to generate several quantitative measures of the spot's size and intensity. Several of these (integrated intensity and the "channel integrals") involve integrations of pixel values, which in the present hardware configurations are proportional to the transmittance of light through the gel area represented by the pixels. A well-known law in spectrophotometry-Beer's law—however, stipulates that the concentration of a light-absorbing substance in solution is proportional to the degree of absorbance, not transmittance, of light passing through the solution. Absorbance is related to transmittance by the relation $A = -\log T$ where T is the fraction of incident light that is transmitted through the medium under examination. In order to achieve linearity between an integrated spot intensity and the physical quantity of protein present in a spot, it is necessary to effect such a transform prior to the integration step. This is done in the software via a lookup table that is generated once (by the TBLGEN routine) when the program is invoked. In order to achieve a reasonably broad and smooth scaling between A and T, the $i^{th}$ table entry is computed as $A(i) = 45.986 \ln(256)$; thus for a pixel value of zero ($i=1$), an absorbance value of 255 is taken from the table, while an input value of 255 (i=256) yields an output value of zero. As shown in FIG. 17, high transmission values tend to be compressed in their absorbance mapping while low values are spread apart. It should be noted at this point that while the integrated intensity and channel integral numbers reported by the system are based on absorbance-transformed pixel values, the spot and background signatures that are provided with them currently are not.

All of the measures calculated for spots by QSPOT are listed with explanation below:

(1) The SPOT CENTROID is calculated as the "center of gravity" of the spot area, with all spot pixels given uniform weighting.

(2) The SPOT SIGNATURE is calculated for each image channel as the mean of the values of pixels lying within a 3×3 pixel box with its center at the spot centroid.

(3) The HEIGHT and WIDTH are lengths of the Y and X sides, respectively, of the minimum enclosing rectangle.

(4) The AREA of a spot is simply the number of pixels contained within it.

(5) The CHANNEL INTEGRAL, which is computed for each image channel, is the absolute value of the difference between each pixel value and the background signature (both absorbance-transformed) summed over all pixels in the spot.

Figure 19:
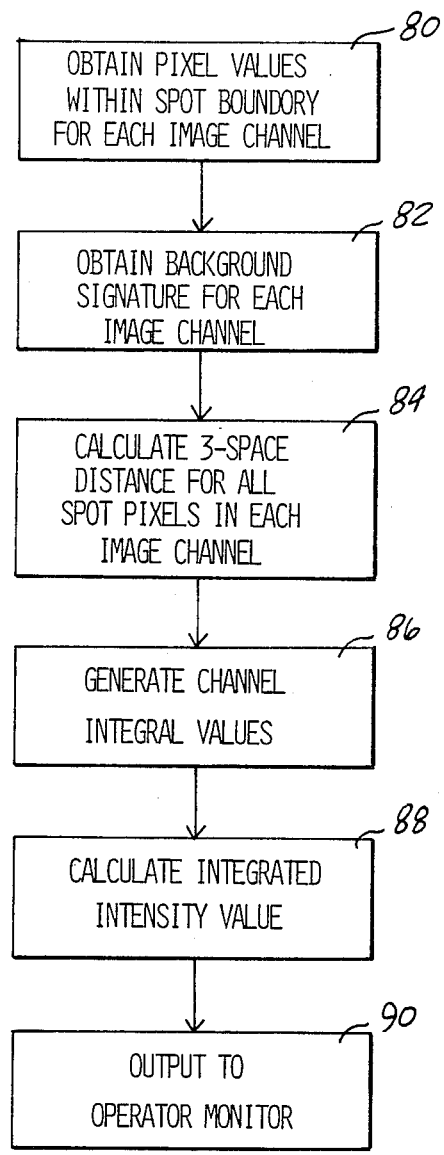
FIG. 19 is a flowchart illustrating the sequence of steps carried out in obtaining spot intensity values.
Figure 18A:
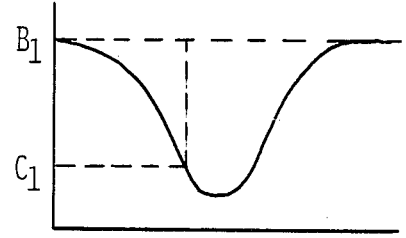
FIG. 18(a-c) are three profiles, each representing pixel values in one of the three image channels.
Figure 18B:
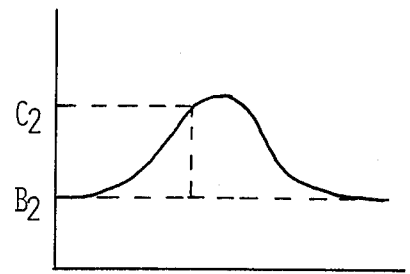
Figure 18C:
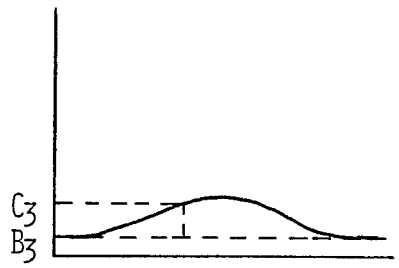

(6) The INTEGRATED INTENSITY, which is the primary measure used to quantify spots, is the INTENSITY of each pixel summed over all of the pixels within the spot. The INTENSITY of a pixel at position (i,j) is defined mathematically as $$I(i,j) = \sum {}^*_K (C_K(i,j) - B_K)^2$$

where $N_c$ is the number of channels in the image, $C_K(i,j)$ is the absorbance-transformed value of the pixel at (i,j) in channel K, $B_K$ is the background signature in channel K, and $*_K$ is a weighting factor for channel K. It can be seen that this is the "distance" between the pixel value and the background signature in the $N_c$-dimensional space defined by the number of channels ($N_c = 3$ for color gels). The coefficients are then dimension-scaling factors that may be used to optimize the intensity measure or to normalize for different light sources and staining techniques. FIGS. 18 and 19 illustrate the computation of intensity for a pixel in a 3-channel image. For example, if $B_1 = 210$, $B_2 = 80$, $B_3 = 10$ and $C_1 = 70$, $C_2 = 180$, $C_3 = 40$; then $$I = (70 - 210)^2 + (180 - 80)^2 + (40 - 10)^2 = 174.6$$

SUMMARY

From the foregoing those skilled in the art will appreciate that the present invention provides significant improvements in this technological art. The system of the present invention enables the researcher to generate accurate and consistent data relating to the analysis of electrophoretograms while requiring only minimal operator interaction. It should be understood that while this invention has been described in connection with the particular examples thereof, those skilled in the art will realize that other modifications can be made thereto without departing from the spirit of this invention after a study of the specification drawings and following claims.

I claim:

1. A method of analyzing electrophoresis samples having a plurality of spots therein, said method comprising:
    displaying an image of at least a portion of said sample on a display;
    selecting a spot on the display desired to be analyzed;
    scanning the sample to generate an electrophoretogram having a matrix of pixel values associated with characteristics of the gel;
    choosing pixel locations within the matrix to define boundary edges for the spot as a function of pixel values located in a predetermined area around the spot;
    analyzing the pixel values within the defined spot boundary and providing output data as a result of the analysis; and
    superimposing over the originally selected spot on the display a visual indication of said chosen pixel locations whose associated values were actually used in be analysis to arrive at said output data thereby providing the user with visual confirmation that the desired spot shape was analyzed.

2. The method of claim 1 wherein said spot boundary is defined by the steps of:
    generating a first plurality of polar cross-sections with values associated with linear segments taken at various angles passing through the cursor-selected spot;
    generating a second plurality of curves as a function of the derivative of the first plurality of polar cross-sections; and,
    selecting those pixel positions associated with given points on the second curves as the boundary edges for the spot.

3. The method of claim 2 wherein the user provides input data to modify the selection of the edge points whereby the size of the spot actually analyzed may more closely match the user's visual analysis.

4. The method of claim 1 wherein said electrophoretogram is represented by three separate image channels formed by scanning a color silver stained electrophoresis gel through different color filters, and wherein the method includes the steps of:
    generating, for each image channel, a histogram of pixel values within a preselected area surrounding the cursor;
    calculating a background signature value for each image channel;
    calculating for each image channel a central signature of the spot as a function of pixel values immediately adjacent said cursor; and,
    selecting the image channel having the greatest difference between the background and central signatures to define the boundary pixel positions of the spot.

5. A method of generating analytical data associated with the protein content of spots in electrophoretograms, said method comprising:
    scanning a color silver stained electrophoresis gel through three different color filters to thereby generate three distinct image channels;
    defining a boundary of a spot desired by be analyzed;
    calculating, for each image channel, a background signature value;
    calculating the relative difference between the background value and the pixel value for each pixel position within the defind spot boundary in the first image channel;

calculating the relative difference between the background value and the pixel value for each pixel position within the defined spot boundary in the second image channel;

calculating the relative difference between the background value and the pixel value for each pixel position within the defined spot boundary in the third image channel;

generating an intensity value for each pixel position in the defined spot as a function of the calculated difference values for that position in each channel; and outputtting an integrated intensity value as a function of the sum of the intensity values for each pixel position within the spot boudnary.

6. A system for analying spots in electrophoretogram image represented by a matrix of pixel values, said system comprising:

a user interactive video display;

manually actuable means for positioning a cursor or the like within a selected spot on the display that is desired to be analyzed;

digital processing means including:

first means for defining a boundary for the spot as a function of characteristics of pixel values adjacent the cursor;

second means for analyzing the pixel values within the defined spot boundary and generating output data relating to the results of the analysis; and third means, responsive to the definition of the spot boundary by the first means, for superimposing over the originally selected spot on the display a visual indication of the locations of the pixel values which were actually analyzed by the second means thereby providing the user with visual confirmation that the second means has analyzed all the pixel values associated with the shape of the spot desired to be analyzed by the user.

7. The system of claim 6 wherein said third means is operative to change the color of all pixel positions within the spot boundary defined by the control means whereby to provide a highlighted overlay on the video display.

8. The system of claim 6 wherein said electrophoretogram is represented in color on the video display by three composite image channels formed by scanning an electrophoresis gel through three different color filters, with the second means being adapted to generate spectral signatures for a central area of the spot closely adjacent the cursor and a background signature for each image channel.

9. The system of claim 8 wherein said second means generates a histogram of the pixel values surrounding the selected spot and selects as background that pixel value associated with a peak in the histogram that is greater than a certain percentage of the tallest peak therein.

10. The system of claim 9 wherein said first means is adapted to select the image channel having the greatest difference between the central and background spectral signatures to define the boundary of the spot.

11. The system of claim 10 wherein said first means is operative to generate a set of interpolative values associated with polar cross-sections through the selected spot and to select points on said cross-sections as a function of derivative characteristics thereof to define the spot boundary.

12. The system of claim 10 which further comprises: input means to allow the user to modify criteria for defining the spot edge boundary whereby the user may alter the selection of said points so that the size of the spot actually analyzed more closely matches the user's visual analysis.

13. The system of claim 8 wherein said second means is operative to provide output data, for each image channel, that is a function of the relative difference between the background signature and pixel values within the spot boundary.

14. The system of claim 8 wherein second means is operative to generate as said output data a value associated with the intensity of the selected spot.

15. The system of claim 14 wherein second means is adapted to generate said intensity output data by calculating an intensity value for each pixel position within the defined spot boundary for each image channel, said intensity value being associated with the three space distance between each pixel value and the background in each image channel and then summing together the intensity values for each pixel position within the spot boundary in each image channel whereby said intensity output data represents an expression of protein content within the spot.

* * * * *